United States Patent
Scheuermann et al.

(10) Patent No.: US 9,220,818 B2
(45) Date of Patent: Dec. 29, 2015

(54) MEDICAL DEVICES HAVING INORGANIC BARRIER COATINGS

(75) Inventors: Torsten Scheuermann, Munich (DE); Michael Kuehling, Munich (DE); Jan Weber, Maastricht (NL); Dominique Seidel, Munich (DE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1350 days.

(21) Appl. No.: 12/501,671

(22) Filed: Jul. 13, 2009

(65) Prior Publication Data

US 2010/0021523 A1 Jan. 28, 2010

Related U.S. Application Data

(60) Provisional application No. 61/082,879, filed on Jul. 23, 2008.

(51) Int. Cl.
| | | |
|---|---|---|
| A61F 2/82 | (2013.01) |
| A61K 9/22 | (2006.01) |
| A61L 27/34 | (2006.01) |
| A61L 31/16 | (2006.01) |
| A61L 31/08 | (2006.01) |
| A61L 31/14 | (2006.01) |

(52) U.S. Cl.
CPC ............... *A61L 31/16* (2013.01); *A61L 31/082* (2013.01); *A61L 31/146* (2013.01); *A61L 2300/608* (2013.01); *A61L 2420/08* (2013.01)

(58) Field of Classification Search
None
See application file for complete search history.

(56) References Cited

U.S. PATENT DOCUMENTS

| | | | |
|---|---|---|---|
| 4,407,695 A | 10/1983 | Deckman et al. | |
| 5,681,196 A | 10/1997 | Jin et al. | |
| 6,504,292 B1 | 1/2003 | Choi et al. | |
| 6,780,491 B1 | 8/2004 | Cathey et al. | |
| 7,169,177 B2 | 1/2007 | Obara | |
| 7,169,178 B1 | 1/2007 | Santos et al. | |
| 2003/0033007 A1* | 2/2003 | Sirhan et al. | 623/1.42 |
| 2006/0004437 A1 | 1/2006 | Jayaraman | |
| 2006/0125144 A1* | 6/2006 | Weber et al. | 264/309 |
| 2006/0193886 A1 | 8/2006 | Owens et al. | |

FOREIGN PATENT DOCUMENTS

| | | |
|---|---|---|
| JP | 2005-328893 | 12/2005 |
| JP | 2008-500121 | 1/2008 |
| WO | WO2006/063157 | 6/2006 |
| WO | WO2007/002133 | 1/2007 |
| WO | WO2008/061017 | 5/2008 |
| WO | WO2008/140482 | 11/2008 |

OTHER PUBLICATIONS

International Preliminary Report on Patentability issued by the WIPO on Feb. 3, 2011, for PCT application: PCT/US2009/050365, filed on Jul. 13, 2009.
International Search Report in International Application No. PCT/US2009/050365, dated Jul. 28, 2010, 6 pages.
International Written Opinion in International Application No. PCT/US2009/050365, dated Jan. 23, 2011, 10 pages.

* cited by examiner

Primary Examiner — H. Sarah Park
(74) Attorney, Agent, or Firm — Fish & Richardson P.C.

(57) ABSTRACT

Medical devices having a barrier layer comprising an inorganic material. The medical device has a reservoir containing a therapeutic agent and the barrier layer is disposed over the reservoir. In one aspect, the barrier layer has one permeability to the therapeutic agent at one portion of the medical device and a different permeability at another portion of the medical device. In another aspect, the dosage amount of the therapeutic agent in the reservoir at one portion of the medical device is different from the dosage amount of the therapeutic agent in the reservoir at another portion of the medical device. In another aspect, a bioresorbable layer is disposed over the barrier layer at one or more portions of the medical device, wherein the bioresorbable layer comprises a bioresorbable material. Also, methods of coating a medical device are disclosed, in which a barrier layer over a medical device is formed using a lithographic etching process where a plurality of particles serve as an etch mask.

15 Claims, 6 Drawing Sheets

MEDICAL DEVICES HAVING INORGANIC BARRIER COATINGS

CROSS REFERENCE TO RELATED APPLICATION

The present application claims priority to U.S. provisional application Ser. No. 61/082,879 filed Jul. 23, 2008, the disclosure of which is incorporated herein by reference in its entirety.

TECHNICAL FIELD

The present invention relates to medical devices, and in particular, medical devices having a coating containing a therapeutic agent.

BACKGROUND

Many implantable medical devices are coated with drugs that are eluted from the medical device upon implantation. For example, some vascular stents are coated with a drug which is eluted from the stent for treatment of the blood vessel and/or to prevent some of the unwanted effects and complications of implanting the stent (e.g., restenosis of the blood vessel). In such drug-eluting medical devices, various methods have been proposed to provide a mechanism for drug elution. However, there is a continuing desire for improved devices and methods for providing drug elution from medical devices.

SUMMARY

In one aspect, the present invention provides a medical device having a reservoir containing a therapeutic agent. In certain embodiments, a barrier layer is disposed over the reservoir, the barrier layer comprising an inorganic material and having a plurality of discontinuities; wherein the permeability of the barrier layer to the therapeutic agent at a first portion of the medical device is greater than the permeability of the barrier layer at a second portion of the medical device.

In certain embodiments, the dosage amount of therapeutic agent contained in the reservoir at a first portion of the medical device is greater than the dosage amount of therapeutic agent contained in the reservoir at a second portion of the medical device; and a barrier layer is disposed over the reservoir, the barrier layer comprising an inorganic material and having a plurality of discontinuities.

In certain embodiments, a barrier layer is disposed over the reservoir, the barrier layer comprising an inorganic material and having a plurality of discontinuities; and a bioresorbable layer is disposed over the barrier layer at one or more portions of the medical device, the bioresorbable layer comprising a bioresorbable material. In some cases, the bioresorbable material is a biodegradable polymer. In some cases, the bioresorbable layer delays the release of the therapeutic agent from the reservoir underlying the bioresorbable layer. In some cases, the bioresorbable layer contains a second therapeutic agent. In some cases, the first therapeutic agent is same as the second therapeutic agent. In some cases, the medical device is a vascular stent, and the bioresorbable layer is disposed over the barrier layer at the end portions of the stent. In some cases, the medical device is a bifurcated vascular stent having a main body and a side-branch portion, and the bioresorbable layer is disposed over the barrier layer at the side-branch portion of the stent. In some cases, the inorganic material is a metallic material.

In another aspect, the present invention provides a method of coating a medical device. In certain embodiments, the method comprises: providing a medical device having a reservoir containing a therapeutic agent; and forming a barrier layer over the reservoir, wherein the step of forming the barrier layer comprises: (a) disposing an inorganic layer over the reservoir, wherein the inorganic layer comprises an inorganic material; (b) applying a contact mask onto the inorganic layer; (c) creating discontinuities in the inorganic layer by etching portions of the inorganic layer using the contact mask; and (d) removing the contact mask.

In some cases, the step of applying a contact mask comprises depositing a plurality of particles onto the inorganic layer. In some cases, the particles form a monolayer on the inorganic layer. In some cases, the particles are electrostatically adhered to the inorganic layer. In some cases, the inorganic material is a metallic material. In some cases, the step of removing the contact mask comprises exposing the contact mask to a solvent. In some cases, the particles are colloidal particles. In some cases, the colloidal particles are deposited onto the inorganic layer by applying a liquid suspension of the colloidal particles onto the inorganic layer. In some cases, the particles are deposited using an electrospray process.

In some cases, the architecture of the contact mask at a first portion of the medical device differs from the architecture of the contact mask at a second portion of the medical device. In some cases, the step of applying a contact mask comprises depositing a plurality of particles onto the inorganic layer, and the packing density of the particles at the first portion of the medical device is greater than the packing density of the particles at the second portion of the medical device. In some cases, the step of applying a contact mask comprises depositing a plurality of particles onto the inorganic layer, and the average size of the particles at the first portion of the medical device is greater than the average size of the particles at the second portion of the medical device. In some cases, the medical device is a vascular stent, and the first portion comprises an intermediate portion of the stent and the second portion comprises the end portions of the stent. In some cases, the medical device is a bifurcated stent having a main body and a side-branch portion, and the first portion comprises the main body and the second portion comprises the side-branch portion of the stent.

In some cases, the reservoir is a polymer layer comprising a polymeric material and the therapeutic agent. In some cases, wherein the step of applying a contact mask comprises: disposing an etchable polymer layer over the inorganic layer; depositing a plurality of particles onto the etchable polymer layer; etching the etchable polymer layer by exposing the etchable polymer layer to an energetic beam to create pillars under the particles; disposing a mask layer over the inorganic layer; and removing the etchable polymer layer and the particles to create the contact mask on the inorganic layer. In some cases, the step of creating discontinuities in the inorganic layer comprises chemically etching portions of the inorganic layer using the contact mask. In some cases, the particles comprise a metallic material.

In certain embodiments, the method comprises: providing a medical device having a reservoir containing a therapeutic agent; and forming a barrier layer over the reservoir, wherein the step of forming the barrier layer comprises: (a) disposing a composite layer over the reservoir, wherein the composite layer comprises a polymeric material and a plurality of particles comprised of an inorganic material; and (b) creating discontinuities in the composite layer by etching portions of the polymeric material in the composite layer using the plurality of particles as a mask.

In some cases, the etching is performed by exposing the composite layer to reactive species. In some cases, the etching is performed by exposing the composite layer to an energetic beam. In some cases, the step of disposing a composite layer over the reservoir comprises depositing the inorganic material and the polymeric material over the reservoir. In some cases, the step of depositing is performed by pulsed laser deposition using a target material comprising a mixture of the inorganic material and the polymeric material. In some cases, the composition of the composite layer at a first portion of the medical device is different from the composition of the composite layer at a second portion of the medical device. In some cases, the particle volume fraction of the composite layer at the first portion of the medical device is greater than the particle volume fraction of the composite layer at the second portion of the medical device. In some cases, the step of disposing a composite layer over the reservoir comprises: depositing a first mixture having a first ratio of inorganic material to polymeric material at the first portion of the medical device; and depositing a second mixture having a second ratio of inorganic material to polymeric material at the second portion of the medical device, wherein the first ratio is greater than the second ratio.

In some cases, the medical device is a vascular stent, and the first portion comprises the end portions of the stent and the second portion comprises an intermediate portion of the stent. In some cases, the medical device is a bifurcated vascular stent having a main body and a side-branch portion, and the first portion comprises the side-branch portion and the second portion comprises the main body. In some cases, the particles comprise a metallic material.

BRIEF DESCRIPTION OF THE DRAWINGS

FIGS. 1A-1C show a stent according to an embodiment of the present invention.

FIGS. 3A and 3B show strut portions of a stent according to yet another embodiment.

FIGS. 4A and 4B show strut portions of a stent according to yet another embodiment.

FIGS. 5A-5D show a method of coating a stent according to yet another embodiment.

FIGS. 6A-6F show a method of coating a stent according to yet another embodiment.

FIGS. 8A and 8B show a method of coating a stent according to yet another embodiment.

DETAILED DESCRIPTION

In one aspect, the present invention provides a medical device having a reservoir containing a therapeutic agent. The reservoir containing the therapeutic agent may be provided in any of various ways. The reservoir may be the therapeutic agent formulation alone, or may comprise any structure that retains or holds the therapeutic agent. For example, the reservoir may be a polymer layer or other type of layer over the medical device, with the therapeutic agent disposed therein. In another example, the reservoir may be created in the surface of the medical device (e.g., a porous surface), or the medical device may have pits, pores, cavities, or holes that contain the therapeutic agent.

Disposed over the reservoir is a barrier layer comprising an inorganic material. The thickness of the barrier layer will vary according to the particular application. For example, for vascular stents, the average thickness of the barrier layer may be in the range of 5 nm to 1000 nm, but other thicknesses are also possible. The inorganic material may be selected on the basis of various considerations, depending upon the particular application. For example, the inorganic material may be selected for its biologic properties, structural properties, chemical properties, handling properties, or the deposition techniques that can be used. Suitable inorganic materials for use in the barrier layer include inorganic elements, such as pure metals including chromium, gold, hafnium, iridium, niobium, palladium, platinum, tantalum, titanium, tungsten, zirconium, and alloys of these metals (e.g., nitinol); and inorganic compounds, such as metal oxides (e.g., iridium oxide or titanium oxide), metal nitrides, and metal carbides, as well as inorganic silicides.

The barrier layer has a plurality of discontinuities. The term "discontinuities," as used herein, refers to pores, holes, openings, cracks, gaps, passages, or other defects through the full thickness of the barrier layer that allow the passage of the therapeutic agent from the reservoir through the barrier layer. These discontinuities may be created using any of various techniques, including direct-write etching using energetic beams (e.g., laser, ion, or electron), micromachining, microdrilling, or lithographic etching processes. Lithographic etching processes that can be used to create the discontinuities include those that use an etch mask formed from a plurality of particles, such as the etching processes described herein.

The size, shape, and dimensions of the discontinuities will vary depending upon the particular application. For example, where the discontinuities are pores, the average diameter of the pores may be in the range of 5 to 1000 nm; and in some cases, in the range of 5 to 500 nm; and in some cases, in the range of 5 to 50 nm. Pores in these size ranges may be useful in providing the desired release characteristics for the therapeutic agent in the treatment of diseased blood vessels.

In certain embodiments, the barrier layer has one permeability to the therapeutic agent at one portion of the medical device and a different permeability at another portion of the medical device. This feature can be useful in providing different release characteristics for the therapeutic agent at different portions of the medical device. The differing permeabilities may be provided by varying the characteristics of the discontinuities at different portions of the medical device. For example, the average size of the discontinuities at one portion of the medical device may be larger than those at another portion of the medical device.

Figure 1A:
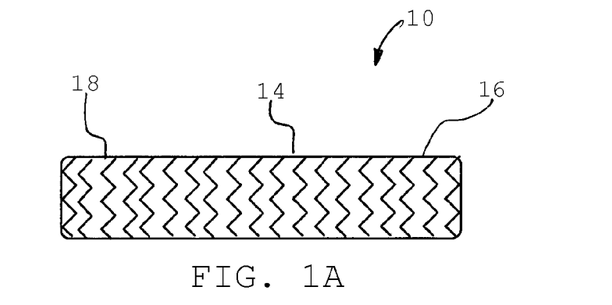
FIG. 1A shows a side view of the stent.
Figure 1B:
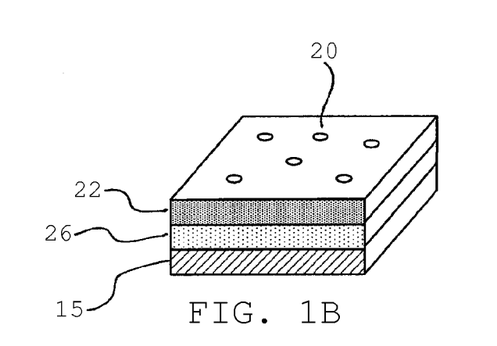
FIG. 1B shows a detailed cross-section perspective view of a strut located at an intermediate portion of the stent.
Figure 1C:
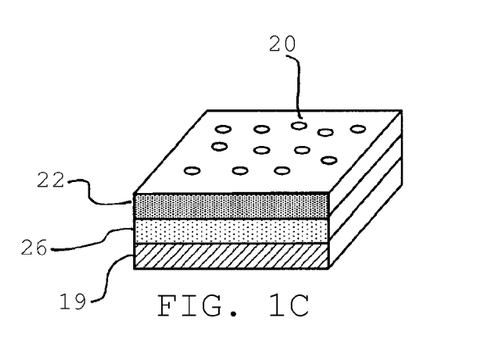
FIG. 1C shows a detailed cross-section perspective view of a strut located at an end portion of the stent.

In another example, referring to the embodiment shown in FIGS. 1A-1C, a vascular stent 10 has a proximal portion 18, a distal portion 16, and an intermediate portion 14. Stent strut 15, shown in FIG. 1B, is located at intermediate portion 14 of stent 10, and stent strut 19 (shown in FIG. 1C) is located at proximal portion 18 or distal portion 16 of stent 10. Stent 10 is coated with a polymer layer 26 formed of a polymeric material, wherein polymer layer 26 contains a therapeutic agent. Polymer layer 26 is coated with a barrier layer 22 comprising an inorganic material. Barrier layer 22 has a plurality of pores 20 which allow the passage of the therapeutic agent from polymer layer 26 through barrier layer 22. To provide differing therapeutic agent release characteristics, barrier layer 22 over stent strut 19 has a higher density of pores 20 than barrier layer 22 over stent strut 15.

In operation, stent 10 is inserted into a blood vessel via a catheter. The higher density of pores at end portions, 16 and 18, of stent 10, provides a higher release rate of the therapeutic agent as compared to the intermediate portion 14 of stent 10. Higher doses of therapeutic agent at the end portions of a stent can be useful in reducing the risk of restenosis that can occur at the end edges of the stent (i.e., "edge effect").

Figure 2:
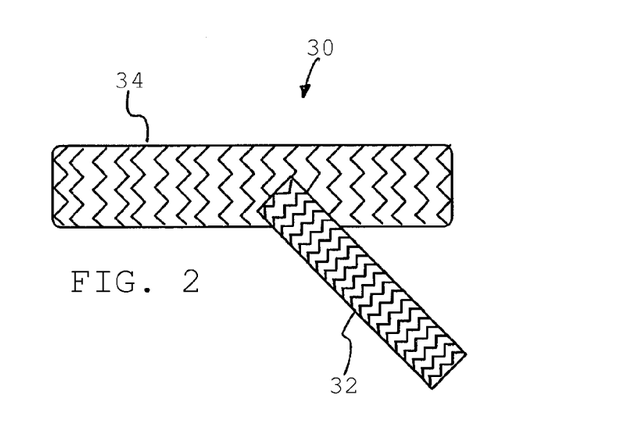
FIG. 2 shows a side view of a bifurcated stent according to another embodiment.

In another example, referring to the embodiment shown in FIG. 2, a bifurcated stent 30 has two portions: a main body 34 for positioning in the main blood vessel, and a side-branch portion 32 for positioning in a side-branch of the main blood vessel. Bifurcated stent 30 is coated with a polymer layer containing a therapeutic agent, which is covered by a barrier layer having a plurality of pores. The barrier layer at side-branch portion 32 has a higher density of pores than the barrier layer at main body 34 of bifurcated stent 30.

In operation, bifurcated stent 30 is inserted via a catheter into a blood vessel at a branch point. The higher density of pores at side-branch portion 32 provides a higher release rate of the therapeutic agent as compared to main body 34 of bifurcated stent 30. Higher doses of therapeutic agent at the side-branch portion of bifurcated stents can be useful in reducing the risk of restenosis in the side-branch of the main blood vessel in bifurcation lesions.

In certain embodiments, the dosage amount of the therapeutic agent in the reservoir at one portion of the medical device is different from the dosage amount of the therapeutic agent in the reservoir at another portion of the medical device. As used herein, "dosage amount" refers to the amount of therapeutic agent that is contained in the reservoir that is disposed over the particular portion of the medical device per unit surface area of the medical device. The differing dosage amounts of the therapeutic agent in the reservoir may be provided in any of various ways. For example, the reservoir may contain a higher concentration of the therapeutic agent at one portion of the medical device than the reservoir at another portion of the medical device.

Figure 3A:
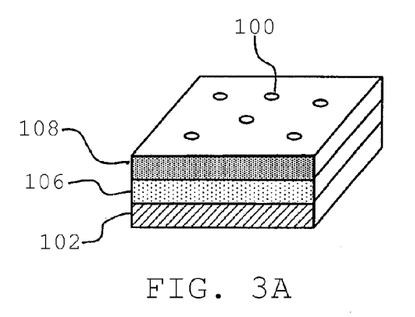
FIG. 3A shows cross-section perspective view of a strut located at an intermediate portion of the stent.
Figure 3B:
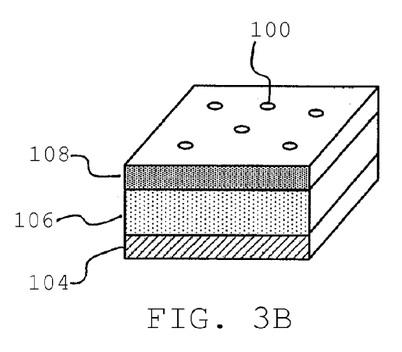
FIG. 3B shows a cross-section perspective view of a strut located at an end portion of the stent.

In another example, referring to the embodiment shown in FIGS. 3A and 3B, a stent (such as one similar to stent 10) has an intermediate portion and end portions (distal and proximal). Stent strut 102, shown in FIG. 3A, is located at the intermediate portion of the stent, and stent strut 104, shown in FIG. 3B, is located at an end portion. The stent is coated with a polymer layer 106 containing a therapeutic agent. Polymer layer 106 over stent strut 104 (end portion) is thicker than polymer layer 106 over stent strut 102 (intermediate portion) such that the end portions of the stent have a higher dosage amount of the therapeutic agent than the intermediate portion of the stent. Polymer layer 106 is coated with a barrier layer 108 formed of an inorganic material. Barrier layer 108 has a plurality of pores 100 to allow the passage of the therapeutic agent contained in polymer layer 106 through barrier layer 108. This stent may be operated in a manner similar to the operation of stent 10, as described above. In an alternate embodiment, the medical device may be a bifurcated stent (such as one similar to bifurcated stent 30) coated with a polymer layer containing a therapeutic agent, with the polymer layer being thicker at the side-branch portion than the main body of the bifurcated stent. A barrier layer, having a plurality of pores, is disposed over the polymer layer.

In certain embodiments, a bioresorbable layer is disposed over the barrier layer at one or more portions of the medical device, wherein the bioresorbable layer comprises a bioresorbable material. As used herein, the term "bioresorbable" is intended to include both biodegradable and bioresorbable. Various types of bioresorbable materials can be used to form the bioresorbable layer, including biodegradable polymers such as those described below. The bioresorbable layer may be used to further control the release of the therapeutic agent from the polymer layer or to provide an additional reservoir of a therapeutic agent.

Figure 4A:
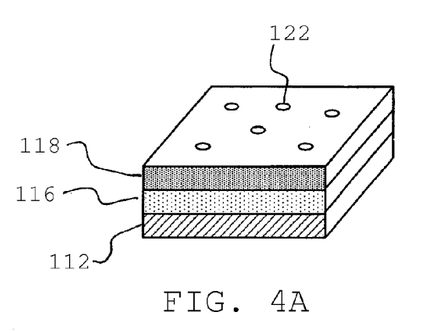
FIG. 4A shows a perspective cross-section view of a strut located at an end portion of the stent.
Figure 4B:
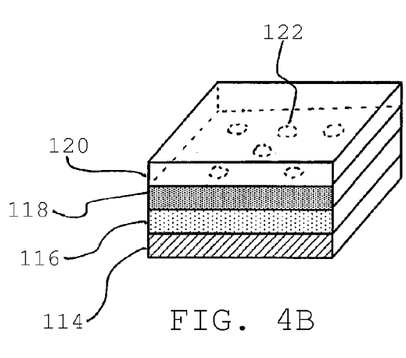
FIG. 4B shows a perspective cross-section view of a strut located at an intermediate portion of the stent.

For example, referring to the embodiment shown in FIGS. 4A and 4B, a stent (such as one similar to stent 10) has a stent strut 112 (FIG. 4A) located at an intermediate portion of the stent and a stent strut 114 (FIG. 4B) located at an end portion of the stent. The stent is coated with a polymer layer 116 containing a therapeutic agent. Polymer layer 116 is coated with a barrier layer 118 formed of an inorganic material. Barrier layer 118 has a plurality of pores 122 to allow the passage of the therapeutic agent contained in polymer layer 116 through barrier layer 118. Barrier layer 118 covering stent strut 114 (end portion) is additionally coated with a bioresorbable layer 120 formed of a biodegradable polymer.

In operation, the stent is inserted into a blood vessel via a catheter. Because of the presence of bioresorbable layer 120 at the end portion of the stent, the release of therapeutic agent from the end portion is initially delayed until bioresorbable layer 120 begins to degrade. This delayed release of the therapeutic agent can be useful in providing treatment in a time-frame that enhances the effectiveness of the therapeutic agent. The length of the delay may be adjusted by varying the degradation rate of bioresorbable layer 120 (e.g., by varying its thickness or composition). In some cases, bioresorbable layer 120 may be designed to degrade at a rate such that the release of the therapeutic agent is delayed for a time period in the range of 5 days to 5 weeks, which is the time range in which the endothelial layer in an artery is re-established after stent treatment.

In an alternate embodiment, bioresorbable layer 120 may contain a therapeutic agent, which may be the same as or different from the therapeutic agent contained in polymer layer 116. This feature may be useful in certain treatment applications by providing an additional release (e.g., a burst release) of the therapeutic agent at the end portions of the stent. In another alternate embodiment, the medical device may be a bifurcated stent (such as one similar to bifurcated stent 30) coated with a polymer layer containing a therapeutic agent, and a barrier layer covering the polymer layer. A bioresorbable layer may cover the barrier layer at the main body or the side-branch portion of the bifurcated stent.

In another aspect, the present invention provides a method of coating a medical device. The method comprises providing a medical device having a reservoir containing a therapeutic agent. The composition and structure of the reservoir are as described above. Further, the method comprises forming a barrier layer over the reservoir using a lithographic etching process with a contact mask to create discontinuities in the barrier layer. The contact mask may comprise a plurality of particles or may be created by using a plurality of particles, wherein the particles are at least partially resistant to degradation under the relevant etching conditions as described below. The particles may comprise any of various materials which are at least partially resistant to degradation under the relevant etching conditions, including metals, ceramics, or polymers. In addition to its resistance to degradation under the etching process, the material used to form the particles can also be selected on the basis of various other considerations, including its electrostatic properties, handling characteristics, or ability to be dispersed in a solvent.

In certain embodiments, the lithographic etching process used to create a barrier layer having discontinuities involves disposing an inorganic layer comprising an inorganic material over the reservoir. The inorganic layer may be applied by depositing the inorganic material using any of various layer deposition processes, including chemical vapor deposition, plasma vapor deposition, sputtering, pulsed laser deposition, sol-gel, evaporation (thermal, electron beam, etc.), molecular beam epitaxy, solution process (e.g., spray coating, dip coating, roll coating, etc.), or electrodeposition (e.g., electroplating, electrospray, etc.).

A plurality of particles are then applied onto the inorganic layer, wherein the plurality of particles constitute a contact mask with apertures being formed by the space between the particles. The apertures in the contact mask expose portions of the inorganic layer in the etching process such that discontinuities are etched into the inorganic layer. The architecture of the contact mask and accordingly, the discontinuities formed in the inorganic layer, will depend upon the characteristics of the particles. These particle characteristics include the size, shape, and dimensions of the particles, which will vary depending upon the particular application. For example, the average diameter of the particles may be in the range of 20 to 1000 nm; and in some cases, in the range of 50 to 250 nm. Particles in these size ranges can be useful for creating discontinuities having sizes for providing therapeutic agent release characteristics suitable for the treatment of diseased blood vessels.

The architecture of the contact mask will also depend on the distribution of the size, shape, and/or dimensions of the particles, as well as the number, spacing, and packing density of the particles, which will vary depending upon the particular application. For example, the particles may be monodisperse or polydisperse with respect to particle size. Monodisperse particles can be used to form discontinuities having more uniform characteristics than those formed using polydisperse particles.

The particles may be arranged in an ordered, semi-ordered, or random fashion. In some cases, the arrangement of the particles will depend upon the characteristics of the surface of the inorganic layer on which the particles are deposited. For example, the particles may be deposited on a textured surface, with the particles following the pattern of the surface texture. The particles may have any of various shapes, including spheroidal or irregular shapes.

The particles may be deposited onto the inorganic layer in any of various ways, including dry deposition and solution processing techniques. For example, the particles may be dispersed in a solution (e.g., as colloidal particles suspended in a liquid) and deposited by spraying or dip-coating techniques. In another example, dry particles may be deposited by electrospray or roll-coating. In some cases, the particles may be deposited in such a manner that a monolayer of the particles are formed on the inorganic layer. For example, a monolayer may be formed by electrostatically charging particles that are made of a dielectric material. The particles can retain some of the electrostatic charge after landing on the inorganic layer, and by mutually repelling forces, cause incoming particles to preferably land into areas with a low density of previously deposited particles. Various other techniques can also be used to create a monolayer of the particles, including using a suspension of colloidal particles that is sufficiently diluted such that the probability of more than one particle being in a sprayed aerosol droplet is very small, or vibrating the substrate to disperse any aggregated particles.

After application of the contact mask, a lithographic etching process is used to etch away portions of the inorganic layer that are exposed by the apertures in the contact mask. Any of various etching processes can be used, including those conventionally used in semiconductor fabrication, such as etching by exposure to energetic beams (e.g., ion beams, electron beams, laser, UV, x-rays) or exposure to reactive species (e.g., plasma, reactive ions, and wet chemicals). The type of process used and the process conditions will depend on various considerations, such as the type of particles being deposited (e.g., their susceptibility to degradation or sputtering under the energetic beam), the thickness and composition of the inorganic layer, or the desired sidewall characteristics of the discontinuities (e.g., anisotropic or isotropic).

The etching process is allowed to continue until the desired discontinuities are formed in the inorganic layer. After the etching process is complete, the particles are removed using any of various techniques, such as brushing, blowing with nitrogen gas, or solvent washing. In some cases, the particles may be removed by another etching process under which the particles are susceptible to degradation. In some cases, where magnetic particles are used, the particles may be removed by magnetic pull.

Figure 5A:
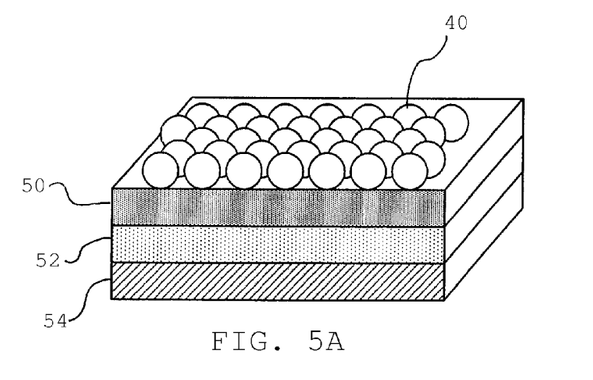
FIG. 5A shows a perspective cross-section view of a strut portion of the stent with a plurality of colloidal particles applied thereon.
Figure 5B:
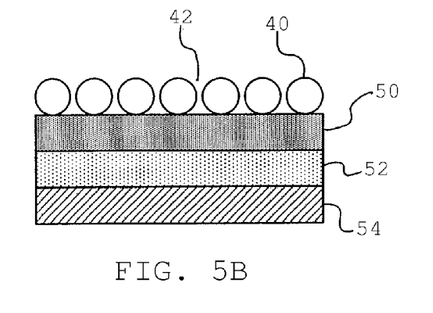
FIG. 5B shows a cross-section side view of the stent strut shown in FIG. 5A.

For example, referring to the embodiment shown in FIGS. 5A-5D, a strut portion 54 of a stent is coated with a polymer layer 52 containing a therapeutic agent. Polymer layer 52 is coated with an inorganic layer 50 formed by depositing an inorganic material onto polymer layer 52. Referring to FIG. 5A, a contact mask is formed by depositing a plurality of monodisperse colloidal gold particles 40 onto inorganic layer 50 by dipping strut portion 54 into a liquid suspension of colloidal particles 40. Colloidal gold particles 40 are electrostatically adhered to inorganic layer 50 and self-assemble into a monolayer on inorganic layer 50. Referring to FIG. 5B, the spaces between colloidal particles 40 form apertures 42 in the contact mask.

Figure 5C:
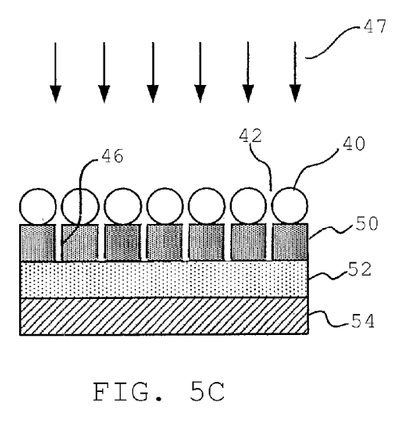
FIG. 5C shows the stent strut of FIG. 5B after undergoing a lithographic etching process.
Figure 5D:
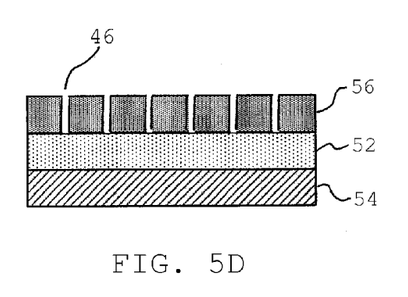
FIG. 5D shows the stent strut of FIG. 5C after removal of the colloidal particles.

Referring to FIG. 5C, using a conventional reactive ion etching apparatus, inorganic layer 50 is exposed to a beam 47 of reactive ions from RF-generated plasma. Colloidal particles 40, which are at least partially etch resistant to the reactive ions, block the reactive ions and thus, serve to protect the underlying portions of inorganic layer 50. The reactive ions that pass through apertures 42 of the contact mask etch away portions of inorganic layer 50 beneath apertures 42 to form pores 46 in inorganic layer 50. After the etching process is completed, as shown in FIG. 5D, colloidal particles 40 are removed by solvent washing, leaving a barrier layer 56 having a plurality of pores 46 which allow the passage of therapeutic agent contained in polymer layer 52.

In some cases, the architecture of the contact mask (including the characteristics and arrangement of its constituent particles) may differ over different portions of the medical device so as to create discontinuities of different sizes or characteristics at the different portions of the medical device. For example, the particles disposed over one portion of the medical device may be larger than those over another portion of the medical device. Where the contact mask is applied using a liquid suspension of colloidal particles, colloidal suspensions having different compositions may be used to apply contact masks having different architectures on different portions of the medical device. For example, one portion of the medical device (e.g., end portions of a stent) may be dipped into a suspension having one concentration and/or size distribution of colloidal particles, and another portion of the medical device (e.g., the intermediate portion of a stent) may be dipped into a suspension having another concentration and/or size distribution of colloidal particles.

Figures 6A, 6B, 6C, 6D, 6E, 6F:
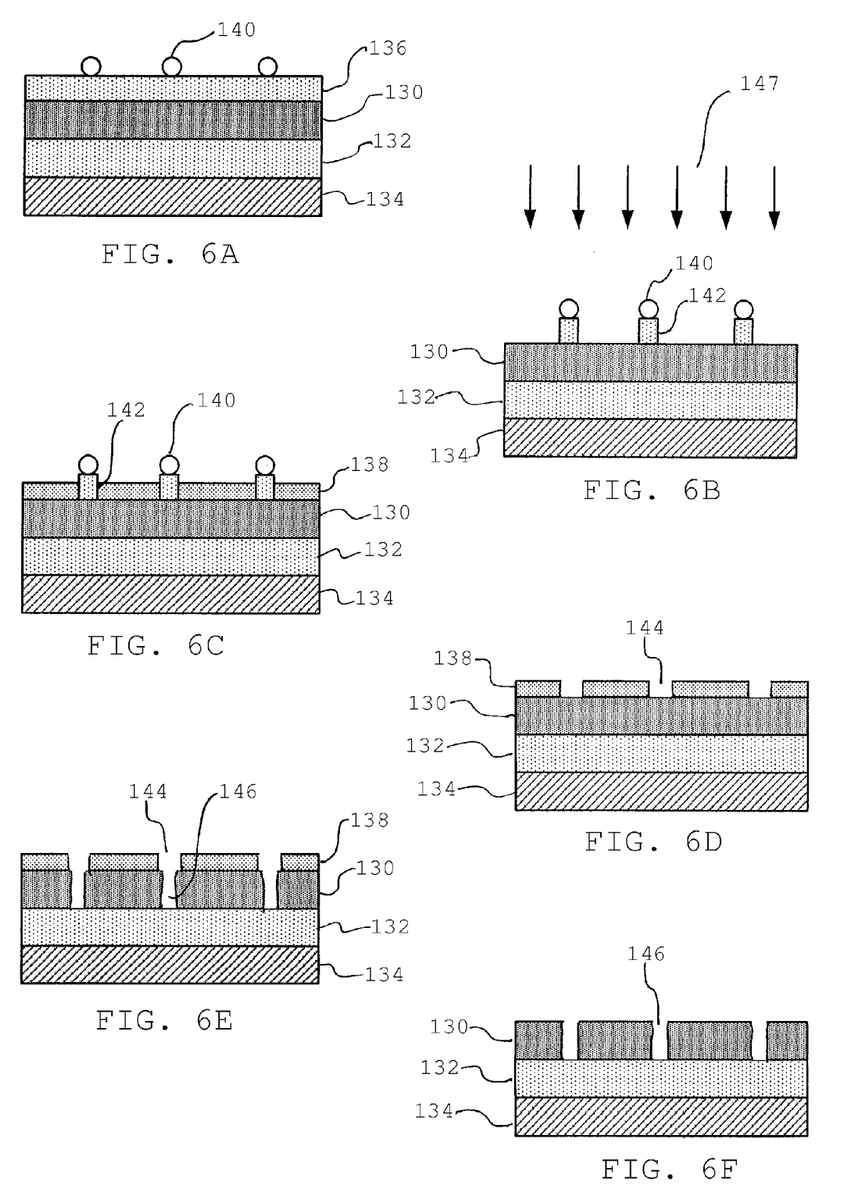
FIG. 6A shows a cross-section side view of a strut portion of the stent prior to laser irradiation.
FIG. 6B shows the strut portion after laser irradiation.
FIG. 6C shows the strut portion after deposition of a mask layer.
FIG. 6D shows the strut portion after removal of the pillars and particles.
FIG. 6E shows the strut portion after chemical etching of the inorganic layer.
FIG. 6F shows the strut portion after removal of the mask layer.

In certain embodiments, instead of serving as the contact mask themselves, the particles are used in creating a contact mask for the barrier layer. As in the above-described embodiments, the architecture of the contact mask may be varied over different portions of the medical device. For example, referring to the embodiment shown in FIGS. 6A-6F, a strut portion 134 of a stent is coated with a first polymer layer 132 containing a therapeutic agent. First polymer layer 132 is coated with an inorganic layer 130 formed by depositing an inorganic material onto first polymer layer 132. Referring to FIG. 6A, a second polymer layer 136 is disposed over inorganic layer 130, wherein second polymer layer 136 is formed of a polymeric material that is etchable by excimer laser. Deposited over second polymer layer 136 is a plurality of metal-coated polystyrene particles 140 having a magnetite kernel (such particles are commercially available). Also, polystyrene particles with gold coating shells are described in Yong et al., "Synthesis and plasmonic properties of silver and gold nanoshells on polystyrene cores of different size and of gold-silver core-shell nanostructures," Colloids & Surfaces, vol. 290, pp. 89-105 (2006). Referring to FIG. 6B, second polymer layer 136 is exposed to a laser beam 147 (e.g., a 195 nm wavelength excimer laser), which etches into second polymer layer 136. But because the laser beam 147 is reflected off the metal coating of polystyrene particles 140, the shadow effect results in the creation of pillars 142 underneath particles 140.

Referring to FIG. 6C, a mask layer 138 is deposited over inorganic layer 130 and in between pillars 142, wherein mask layer 138 is formed of a polymeric material that is resistant to the chemical etching process described below. Referring to FIG. 6D, pillars 142 are removed by solvent dissolution and particles 140 are removed by magnetic pull, resulting in openings 144 in mask layer 138. As such, being etch-resistant, mask layer 138 can now serve as a contact mask for inorganic layer 130. Accordingly, referring to FIG. 6E, a chemical etching process is used to etch pores 146 into inorganic layer 130, in which mask layer 138 serves as the contact mask. Referring to FIG. 6F, after the etching process is complete, removal of mask layer 138 leaves inorganic layer 130 (now a porous barrier layer) with pores 146 which allow the passage of therapeutic agent contained in first polymer layer 132.

In certain embodiments, the lithographic etching process used to create a barrier layer having discontinuities involves disposing a composite layer over the reservoir. The composite layer comprises a polymeric material and the above-described plurality of particles. The particles within the composite layer serve as an etch mask in the etching process to create discontinuities in the composite layer. Thus, the discontinuities created in the composite layer will vary according to the particular characteristics of the particles in the composite layer, including their composition, size, size distribution, shape, dimensions, number, packing density (i.e., number of particles per unit volume of the composite layer), and particle volume fraction (i.e., the total volume of particles per unit volume of the composite layer).

For example, in some cases, the particle volume fraction of the composite layer may be in the range of 10 to 70 percent. Composite layers having this composition may be useful for creating discontinuities having sizes for providing therapeutic agent release characteristics suitable for the treatment of diseased blood vessels. In some cases, the individual particles may be a cluster of sub-particles. The polymeric material, which may comprise any of various polymers, including those described below, is intended to be etchable by the particular etching process used in the method.

The composite layer may be applied using any of various layer deposition processes. For example, layer deposition processes that may be suitable for forming the composite layer include: chemical vapor deposition, plasma vapor deposition, sputtering, pulsed laser deposition, sol-gel, evaporation (thermal, electron beam, etc.), molecular beam epitaxy, solution process (e.g., spray coating, dip coating, roll coating, etc.), or electrodeposition (e.g., electroplating, electrospray, etc.). Roder et al., "Tuning the microstructure of pulsed laser deposited polymer-metal nanocomposites," Applied Physics A, vol. 85:15-20 (2006), describes one such method, using pulsed laser deposition, by which the composite layer may be applied.

The composite layer is then exposed to an etching process to etch away portions of the polymeric material in the composite layer. Depending upon the particular etching conditions, the etching process may be isotropic or anisotropic. Anisotropic etching (e.g., using a unidirectional beam) can be useful where discontinuities having vertically-oriented sidewalls are desired. Isotropic etching (e.g., using wet chemical etching techniques) can be useful in creating a network of pores which are interconnected via channels radiating in various directions.

Figure 7:
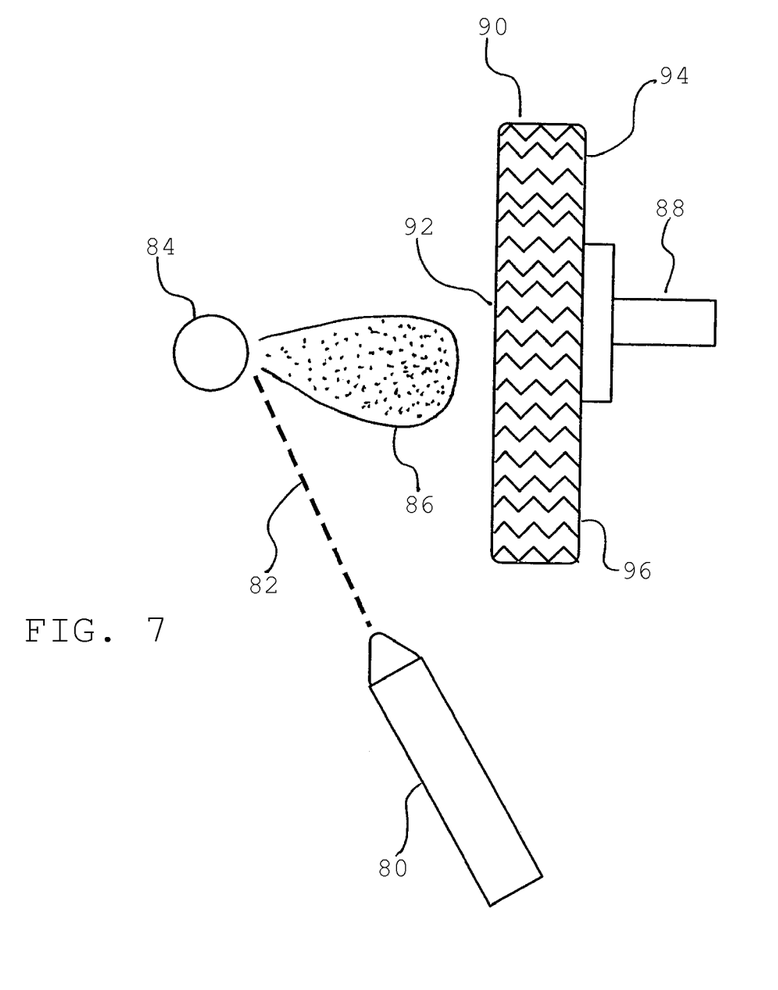
FIG. 7 shows a schematic representation of an apparatus that can be used to deposit a composite layer for implementing a method of coating a stent according to yet another embodiment.

For example, referring to the embodiment shown in FIG. 7, a stent 90 having a polymer layer containing a therapeutic agent is held on a stent holder 88 such that the stent is positioned adjacent to a target material 84. Target material 84 is a mixture of a polymeric material (which may be the same or different from the polymeric material used in the polymer layer on stent 90) and a metallic material, both of which are suitable for pulsed laser deposition. A pulsed laser beam 82 from a high power laser 80 is focused onto target material 84, creating a plume 86 of vaporized material which is deposited onto stent 90. In order to achieve a composite layer having the desired characteristics, various conditions in the pulsed laser deposition process may be adjusted, including the composition of the target material and the power or pulse frequency of the laser.

Figure 8A:
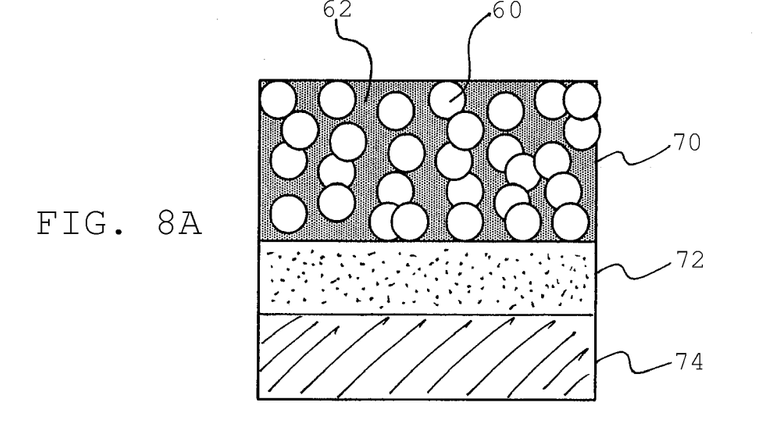
FIG. 8A shows a cross-section side view of a strut portion of the stent before undergoing a lithographic etching process.
Figure 8B:
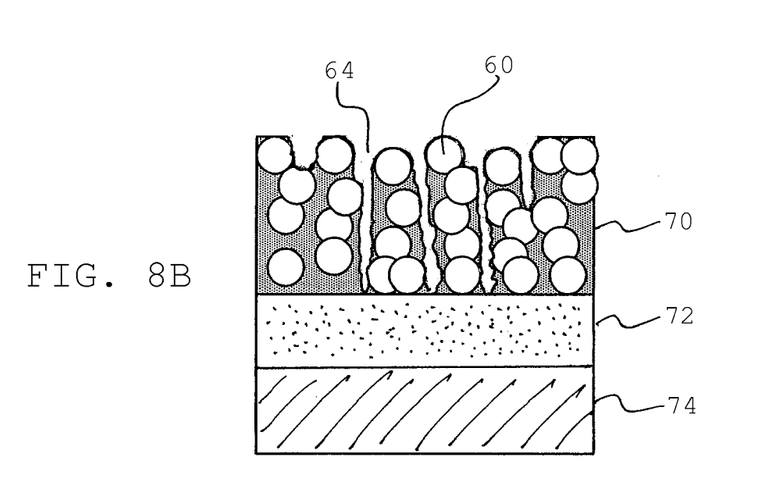
FIG. 8B shows the stent strut of FIG. 8A after the etching process.

As shown in FIGS. 8A and 8B, a strut 74 on stent 90 is coated with polymer layer 72 containing the therapeutic agent. By depositing target material 84 onto polymer layer 72 using pulsed laser deposition, a composite layer 70 is created. Composite layer 70 comprises a polymeric material 62 and metal particles 60 which form by nucleation and growth of the deposited metallic material. Next, composite layer 70 is subjected to a conventional reactive ion etching process which etches away portions of polymeric material 62 that are not protected by particles 60. This etching of polymeric material 62 creates pores 64 in composite layer 70.

In some cases, the composite layer may have a different composition at different portions of the medical device such that the etching process will create discontinuities of varying characteristics at the different portions of the medical device. Composite layers of different compositions may be created by varying the deposition conditions at the different portions of the medical device. For example, when using pulsed laser deposition, different portions of the medical device may be traversed over plumes created from different target materials (e.g., having different ratios of the polymeric material and the metallic material). Thus, for example, referring to FIG. 7, in an alternate embodiment, after pulsed laser deposition of target material 84 onto center portion 92 of stent 90, another target material having a lower ratio of the metallic material is used for pulse laser deposition onto the end portions, 94 and 96, of stent 90. This creates a composite layer having a lower density of the metal particles at the ends portions, 94 and 96, of the stent, which can allow for the creation of larger pores in the composite layer after etching.

Non-limiting examples of medical devices that can be used with the present invention include stents, stent grafts, catheters, guide wires, neurovascular aneurysm coils, balloons, filters (e.g., vena cava filters), vascular grafts, intraluminal paving systems, pacemakers, electrodes, leads, defibrillators, joint and bone implants, spinal implants, access ports, intra-aortic balloon pumps, heart valves, sutures, artificial hearts, neurological stimulators, cochlear implants, retinal implants, and other devices that can be used in connection with therapeutic coatings. Such medical devices are implanted or otherwise used in body structures, cavities, or lumens such as the vasculature, gastrointestinal tract, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone, joints, and the like.

The therapeutic agent used in the present invention may be any pharmaceutically acceptable agent (such as a drug), a biomolecule, a small molecule, or cells. Exemplary biomolecules include peptides, polypeptides and proteins; antibodies; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Exemplary small molecules include hormones, nucleotides, amino acids, sugars, and lipids and compounds have a molecular weight of less than 100 kD. Exemplary cells include stem cells, progenitor cells, endothelial cells, adult cardiomyocytes, and smooth muscle cells.

A reference to an element by the indefinite article "a" or "an" does not exclude the possibility that more than one of the element is present. Rather, the article "a" or "an" is intended to mean one or more (or at least one) unless the text expressly indicates otherwise. The terms "first," "second," and so on, when referring to an element, are not intended to suggest a location or ordering of the elements. Rather, the terms are used as labels to facilitate discussion and distinguish elements from one another.

The foregoing description and examples have been set forth merely to illustrate the invention and are not intended to be limiting. Each of the disclosed aspects and embodiments of the present invention may be considered individually or in combination with other aspects, embodiments, and variations of the invention. Modifications of the disclosed embodiments incorporating the spirit and substance of the invention may occur to persons skilled in the art and such modifications are within the scope of the present invention.

We claim:

1. A medical device comprising:
   a reservoir containing a therapeutic agent;
   a barrier layer disposed over the reservoir, the barrier layer comprising an inorganic material and having a plurality of discontinuities, wherein the barrier layer is permeable to the therapeutic agent, and wherein the permeability of the barrier layer to the therapeutic agent at end portions of the medical device is greater than the permeability of the barrier layer at an intermediate portion of the medical device; and
   a bioresorbable layer over the barrier layer at least one of the end portions of the medical device, wherein the intermediate portion is free of the bioresorbable layer.

2. The medical device of claim 1, wherein the density of discontinuities in the barrier layer at the end portions is greater than the density of the discontinuities at the intermediate portion.

3. The medical device of claim 1, wherein the average size of the discontinuities in the barrier layer at the end portions is greater than the average size of the discontinuities at the intermediate portion.

4. The medical device of claim 1, wherein the medical device is a vascular stent.

5. The medical device of claim 1, wherein the medical device is a bifurcated vascular stent having a main body and a side-branch portion, wherein the first portion comprises the side-branch portion, and wherein the second portion comprises the main body of the stent.

6. The medical device of claim 1, wherein the reservoir is a polymer layer comprising a polymeric material and the therapeutic agent.

7. The medical device of claim 1, wherein the discontinuities in the barrier layer comprise vertically-oriented sidewalls.

8. The medical device of claim 1, wherein the discontinuities are pores having an average diameter in the range of 5 nm to 500 nm.

9. The medical device of claim 1, wherein the inorganic material is a metallic material.

10. A medical device comprising:
    a reservoir containing a therapeutic agent, wherein the dosage amount of therapeutic agent contained in the reservoir at end portions of the medical device is greater than the dosage amount of therapeutic agent contained in the reservoir at an intermediate portion of the medical device;
    a barrier layer disposed over the reservoir, the barrier layer comprising an inorganic material and having a plurality of discontinuities, and
    a bioresorbable layer over the barrier layer at least one of the end portions of the medical device, wherein the intermediate portion is free of the bioresorbable layer.

11. The medical device of claim 10, wherein concentration of the therapeutic agent in the reservoir at the end portions is greater than concentration of the therapeutic agent in the reservoir at the intermediate portion of the medical device.

12. The medical device of claim 10, wherein the reservoir is a polymer layer comprising a polymeric material and the therapeutic agent, and wherein the thickness of the polymer layer is greater at the end portions than at the intermediate portion of the medical device.

13. The medical device of claim 10, wherein the medical device is a vascular stent.

14. The medical device of claim 10, wherein the medical device is a bifurcated vascular stent having a main body and a side-branch portion, and wherein the first portion comprises the side-branch portion and the second portion comprises the main body.

15. The medical device of claim 10, wherein the inorganic material is a metallic material.

\* \* \* \* \*